United States Patent
Burg et al.

(10) Patent No.: US 11,754,823 B2
(45) Date of Patent: Sep. 12, 2023

(54) CRYO-LIGHT MICROSCOPE AND IMMERSION MEDIUM FOR CRYO-LIGHT MICROSCOPY

(71) Applicant: Max-Planck-Gesellschaft zur Foerderung der Wissenschaften e.V., Munich (DE)

(72) Inventors: Thomas P. Burg, Goettingen (DE); Margherita Bassu, Goettingen (DE); Yara Mejia, Berkeley, CA (US); Raffaele Faoro, Goettingen (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 535 days.

(21) Appl. No.: 16/822,173

(22) Filed: Mar. 18, 2020

(65) Prior Publication Data
US 2020/0285036 A1   Sep. 10, 2020

Related U.S. Application Data

(63) Continuation of application No. PCT/EP2018/075333, filed on Sep. 19, 2018.

(30) Foreign Application Priority Data

Sep. 20, 2017   (EP) .................................... 17192011

(51) Int. Cl.
*G02B 21/33* (2006.01)
*C07C 43/12* (2006.01)
(Continued)

(52) U.S. Cl.
CPC .............. *G02B 21/33* (2013.01); *C07C 43/02* (2013.01); *C07C 43/12* (2013.01); *C09K 5/10* (2013.01)

(58) Field of Classification Search
None
See application file for complete search history.

(56) References Cited

U.S. PATENT DOCUMENTS

5,181,382 A    1/1993  Middlebrook
5,713,211 A *  2/1998  Sherwood ............. F25B 25/005
                                                     252/67

(Continued)

FOREIGN PATENT DOCUMENTS

DE    10 006 034 534 A1    1/2008
DE    10 2014 017 287 A1   6/2015

(Continued)

OTHER PUBLICATIONS

Chinese Office Action in related, co-pending Chinese application No. CN 201880061374.0, dated Jun. 1, 2021.

(Continued)

*Primary Examiner* — Ellen M McAvoy
(74) *Attorney, Agent, or Firm* — Thomas | Horstemeyer, LLP

(57) ABSTRACT

Ethoxy-nonafluorobutane ($C_4F_9OC_2H_5$) is used as an immersion medium for immersing an immersion objective of a cryo-light microscope. The cryo-light microscope comprising an immersion objective, a front lens mount holding a front lens of the immersion objective, a sample holder and a cold stage carrying the sample holder further has a heating device coupling a heat flow into the front lens mount.

9 Claims, 11 Drawing Sheets

(51) Int. Cl.
C09K 5/10 (2006.01)
C07C 43/02 (2006.01)

(56) References Cited

U.S. PATENT DOCUMENTS

| | | | |
|---|---|---|---|
| 5,819,549 | A | 10/1998 | Sherwood |
| RE37,054 | E | 2/2001 | Sherwood |
| RE37,119 | E | 4/2001 | Sherwood |
| 6,836,131 | B2 | 12/2004 | Cader et al. |
| 7,382,531 | B2 | 6/2008 | Tsuchiya et al. |
| 7,502,165 | B2 | 3/2009 | Wehner et al. |
| 7,660,054 | B2 | 2/2010 | Wagner et al. |
| 8,144,406 | B2 | 3/2012 | Wadell et al. |
| 9,512,460 | B2 | 12/2016 | Mayer et al. |
| 9,784,962 | B2 | 10/2017 | Ingersoll et al. |
| 2006/0250591 | A1* | 11/2006 | Straaijer ............ G03F 7/70341 355/53 |
| 2009/0010629 | A1* | 1/2009 | Vondracek ............ G03B 43/00 396/25 |
| 2019/0048204 | A1* | 2/2019 | Bejanin ................ C23C 22/03 |
| 2019/0337933 | A1* | 11/2019 | Bulinski ................ C09K 5/10 |
| 2020/0178414 | A1* | 6/2020 | Bulinski ............... C07C 211/24 |
| 2020/0285036 | A1* | 9/2020 | Burg ....................... C09K 5/10 |

FOREIGN PATENT DOCUMENTS

| | | |
|---|---|---|
| EP | 0856038 A1 | 8/1998 |
| EP | 1 870 752 A1 | 12/2007 |
| SU | 1 016 641 | 5/1983 |
| WO | 97/014762 | 4/1997 |
| WO | 2006/113916 A2 | 10/2006 |
| WO | WO-2006113916 A2 * | 10/2006 ............ G02B 21/28 |

OTHER PUBLICATIONS

Kaufmann, R. et al. "Fluorescence cryo-microscopy: current challenges and prospects", Curr. Opin. Chem. Biol. 20, 86-91 (2014) (http://www.sciencedirect.com/science/article/pii/S1367593114000623).
Schwartz, C. L. et al. "Cryofluorescence microscopy facilitates correlations between light and cryoelectron microscopy and reduces the rate of photobleaching", J. Microsc. 227, 98-109 (2007).
Kaufmann, R. et al. "Super-Resolution Microscopy Using Standard Fluorescent Proteins in Intact Cells under Cryo-Conditions", Nano Lett. 14, 4171-4175 (2014). (http://pubs.acs.org/doi/abs/10.1021/nl501870p).
Moerner, W. E. et al. "Illuminating single molecules in condensed matter", Sci. (New York, N.Y.) 283, 1670-6 (1999). (http://www.ncbi.nlm.nih.gov/pubmed/10073924).
Kozankiewicz, B. et al. "Singlemolecule photophysics, from cryogenic to ambient conditions", Chem. Soc. Rev. 43, 1029-1043 (2014). (http://xlink.rsc.org/?DOI=C3CS60165J).
Li, W. et al. "Ultra-stable and versatile widefield cryo-fluorescence microscope for single-molecule localization with sub-nanometer accuracy", Opt. express 23, 3770-83 (2015). (http://www.osapublishing.org/viewmedia.cfm?uri=oe-23-3-3770&seq=0&html=true).
Metzger, M. et al. "Resolution enhancement for low-temperature scanning microscopy by cryoimmersion", Opt. Express 24, 13023 (2016). (https://www.osapublishing.org/abstract.cfm?URI=oe-24-12-13023).
Hell, S. W. et al. "Breaking the Diffraction Resolution Limit By Stimulated-Emission—Stimulated-Emission-Depletion Fluorescence Microscopy", Opt. Lett. 19, 780-782 (1994).
Betzig, E. et al. "Imaging Intracellular Fluorescent Proteins at Nanometer Resolution", Sci. 313, 1642-1645 (2006). (http://www.sciencemag.org/cgi/doi/10.1126/ science.1127344).
Gustafsson, M. G. L. "Surpassing the lateral resolution limit by a factor of two using structured illumination microscopy", J. Microsc. 198, 82-87 (2000).
Sartori, A. et al. "Correlative microscopy: Bridging the gap between fluorescence light microscopy and cryo-electron tomography", J. Struct. Biol. 160, 135-145 (2007). (http://linkinghub.elsevier.com/retrieve/pii/S1047847707001724).
Agronskaia, A. V. et al. "Integrated fluorescence and transmission electron microscopy", J. Struct. Biol. 164, 183-189 (2008). (http://dx.doi.org/10.1016/j.jsb.2008.07.003).
Smith, E. A. et al. "Quantitatively Imaging Chromosomes by Correlated Cryo-Fluorescence and Soft X-Ray Tomographies", Biophys. J. 107, 1988-1996 (2014). (http://linkinghub.elsevier.com/retrieve/pii/S0006349514009497).
Chang, Y.-W. et al. "Correlated cryogenic photoactivated localization microscopy and cryo-electron tomography", Nat. Methods 11, 737-739 (2014). (http://www.nature.com/doifinder/10. 1038/nmeth.2961).
Liu, B. et al. "Three-dimensional super-resolution protein localization correlated with vitrified cellular context", Sci. Reports 5, 13017 (2015). (http://www.nature.com/articles/srep13017).
Nahmani, M. et al. "High-numericalaperture cryogenic light microscopy for increased precision of superresolution reconstructions", Proc. Natl. Acad. Sci. 114, 3832-3836 (2017). (http://www.pnas.org/lookup/doi/10.1073/pnas.1618206114).
Schorb, M. et al. "Correlated cryofluorescence and cryo-electron microscopy with high spatial precision and improved sensitivity", Ultramicroscopy 143, 24-32 (2014). (http://dx.doi.org/10.1016/j.ultramic.2013.10.015).
Arnold, J. et al. "Site-Specific Cryofocused Ion Beam Sample Preparation Guided by 3D Correlative Microscopy", Biophys. J. 110, 860-869 (2016). (http://linkinghub.elsevier.com/retriev e/pii/S0006349515011637).
Schorb, M. et al. "New hardware and workflows for semi-automated correlative cryo-fluorescence and cryo-electron microscopy/tomography", J. Struct. Biol. 197, 83-93 (2017). (http://linkinghub.elsevier.com/retrieve/pii/S1047847716301356).
Le Gros, M. et al. "High-aperture cryogenic light microscopy", Journal of Microscopy, vol. 235, No. 1, 1-8 (2009), XP055482928, ISSN: 0022-2720.
Smith, E. A. et al. "Correlative cryogenic tomography of cells using light and soft x-rays", Ultramicroscopy 143, 33-40 (2014). (http://dx.doi.org/10.1016/j.ultramic.2 013.10.013).
Edelstein, A. D. et al. "Advanced methods of microscope control using μManager soft-ware", J. Biol. Methods 1, 10 (2014). (http://www.jbmethods.org/jbm/article /view/36).
Schindelin, J. et al. "Fiji: an opensource platform for biological-image analysis" Nat. Methods 9, 676-682 (2012). (http://www.ncbi.nlm.nih.gov/pubmed /22743772).
Sage, D. et al. "DeconvolutionLab2: An open-source software for deconvolution microscopy", Methods 115, 28-41 (2017). (http://linkinghub.elsevier.com/retrieve/pii/ S1046202316305096).
Thevenaz, P. et al. "A pyramid approach to subpixel registration based on intensity", IEEE Transactions on Image Process. 7, 27-41 (1998). (http://ieeexplore.ieee.org/document/ 650848/).
Nasse, M. J. et al. "Realistic modeling of the illumination point spread function in confocal scanning optical microscopy", J. Opt. Soc. Am. A 27, 295 (2010). (https://www.osapublishing.org/abstract.cfm?URI=josaa-27-2-295).
Derosier: "Cryo-PALMing the Synapse. The M.R. Bauer Foundation Colloquium Series", Annual Scientific Retreat and Distinguished Lecturer Series, Brandeis University, Benjamin and Mae Volen National Center for Complex Systems, Aug. 1, 2011, XP055253191.
Hagiwara, T. et al. "Sub-40 nm pattern fabrication in 157 nm interferometric immersion lithography", Spie 31st International Symposium on Advanced Lithography, Feb. 19-24, 2006, Proceedings of Spie, vol. 6154, Mar. 21, 2006, XP002779400, ISSN: 0277-786X.
3M: "3M Novec 7200 Engineered Fluid", Internet Citation, Aug. 30, 2005, XP002779401, (https://multimedia.3m.com/mws/me dia/1998190/3mtm-novectm-7200- engineered-fluid.pdf).
Li, De-Sheng et al. "Detection of sitedependent segmental mobility of polymer by fluorescent defocused imaging"; Chinese Journal of Polymer Science, vol. 35, No. 12 (2017), 1488-1496, XP036348150.

(56) References Cited

OTHER PUBLICATIONS

Shi, Yu et al. "Photo-controllable coilto- globule transition of single polymer molecules"; Polymer, Elsevier Science Publishers B.V., GB, vol. 97 (2016) 309-313, XP029634975.

* cited by examiner

Im. Obj. HFE 7200, -140 °C

Simulated PSF for n=1.334

Im. Obj. HFE 7200, -130 °C

Simulated PSF for n=1.329

Im. Obj. HFE 7200, -90 °C

Simulated PSF for n=1.310

CRYO-LIGHT MICROSCOPE AND IMMERSION MEDIUM FOR CRYO-LIGHT MICROSCOPY

CROSS REFERENCE TO RELATED APPLICATIONS

This application is a continuation to International Application PCT/EP/2018/075333 with an international filing date of Sep. 18, 2018 entitled "CRYO-LIGHT MICROSCOPE AND IMMERSION MEDIUM FOR CRYO-LIGHT MICROSCOPY" and claiming priority to European Patent Application No. EP 17 192 011.9 entitled "CRYO-LIGHT MICROSCOPE AND IMMERSION MEDIUM FOR CRYO-LIGHT MICROSCOPY" and filed on Sep. 20, 2018.

FIELD OF THE INVENTION

The present invention relates to an immersion medium for immersing an immersion objective in light microscopy. More particularly, the invention relates to a cryo-immersion medium suitable for use in cryo-light microscopy in which a sample to be imaged is kept at a cryogenic temperature.

Further, the present invention relates to a cryo-light microscope.

BACKGROUND OF THE INVENTION

Cryogenic fluorescent light microscopy of flash-frozen cells stands out by artifact free fixation and very little photobleaching of the fluorophores used. To attain the highest level of resolution, aberration-free immersion objectives with accurately matched immersion media are required, but both do not exist for imaging below the glass transition temperature of water.

Fluorescent light microscopy at cryogenic temperature presents significant advantages in itself and provides an important complement to electron cryomicroscopy.[1] In particular, bleaching decreases drastically at low temperature[2] while the fluorescence yield of many fluorophores increases[3] and the spectral bands narrow.[4-7] The application of modern super-resolution methods such as STED[8], PALM[9], STORM, or SIM[10] at cryogenic temperature holds the prospect of imaging fluorescent proteins with molecular resolution in 3D and correlating their localization with the ultrastructure seen in electron cryomicroscopy of the same sample.[2, 3, 11-16] In contrast to chemical fixation, cryofixation provides an unbiased, undistorted representation of the native state. This is increasingly more important as imaging resolution approaches the nanometer scale.

A long-standing challenge in cryogenic light microscopy is the lack of high-numerical aperture (NA) microscope objectives. The numerical aperture of an objective is the primary figure of merit that dictates its light collection efficiency and diffraction-limited resolution. Significant technological development has been devoted towards user-friendly platforms based on high-NA air objectives optimized for cryomicroscopy.[17-19] However, air objectives are fundamentally limited to NA values less than 1.

Immersion objectives can surpass this limit by making physical contact with the sample via an immersion medium of refractive index greater than 1. At room temperature, this is a cornerstone of practically all high-resolution light microscopy, but for imaging below the glass transition of water ($\sim -135°$ C.), no satisfactory counterpart exists.

Only an immersion medium suitable for temperatures below $-135°$ C. will allow for imaging a high pressure frozen water containing biological samples without altering the structure of the frozen water or the sample therein. Above this temperature, the amorphous water in the sample will convert into crystalline water. This conversion will affect the sample due to the increased volume of crystalline water and due to alterations in solubility of biological molecules in crystalline and amorphous states of solid water; it will also change the optical properties of the sample.

In particular, an immersion medium for temperatures below $-135°$ C. having a refractive index close to that of liquid water at room temperature is required for aberration-free imaging at different depths in high pressure frozen or plunge frozen water containing biological samples. This particularly applies to parts of such a sample which are located below the surface of the sample in cryo-light microscopy.

Two different approaches towards cryo-immersion light microscopy have been proposed in the past. The first is to cool the sample and the objective to cryogenic temperature, thereby avoiding thermal gradients in the system. This approach was followed by the Larabell-group[20, 21] and by the group of Brecht[7]. Both employed inexpensive oil immersion objectives that could sustain the deep temperature cycles without damage. However, this approach has never been shown to work with sophisticated bio-imaging immersion objectives. These rely on numerous glued and often adjustable lens groups that would require an elaborate re-design for temperatures below $-135°$ C. A second challenge is that no adequate index-matching media are available for this temperature range. Aberration-free imaging requires the refractive index to be within at least $\sim 10^{-3}$ RIU of the design value for the objective (RIU=refractive index unit). In addition, the medium needs to be optically clear, non-fluorescent, non-toxic, and have low vapor pressure at the imaging temperature. Facile storage and handling, moreover, require that the liquid range should extend above room temperature. Although the group of Brecht found that 1-propanol (melting point $-126°$ C.) satisfies many of these criteria at $-110°$ C., this is still significantly above the glass transition of water and cannot be generalized to lower temperatures.

In the second approach described in the literature, the objective remains warm while a temperature drop of >150° C. is maintained between the sample and the front lens. Nahmani et al. accomplished this by injecting a continuous stream of a warm Ethanol/water mixture (70% Ethanol) between the front lens and a coverslip placed on top of the cryogenically cooled sample.[16] Although freezing was successfully prevented, the refractive index of the Ethanol/water mixture did not match the design of the objective. In general, attaining an accurate and stable index-match in this technique is complicated by the presence of thermal boundary layers and the potential for pressure-induced artifacts.

According to https://en.wikipedia.org/wiki/Hydrofluoroether, a hydrofluoroether (HFE) is a complex organic solvent. As a non-ozone-depleting chemical, it was developed originally as a replacement for CFCs, HFCs, HCFCs, and PFCs. HFE does not occur naturally. It is colorless, odorless, tasteless, low toxicity, low viscosity, and liquid at room temperature. It is visually indistinguishable from water at room temperature.

SUMMARY OF THE INVENTION

The present invention relates to an immersion medium for immersing an immersion objective in light microscopy, wherein the immersion medium is essentially made of hydrofluoroether.

The present invention also relates to a use of a cryogenic liquid essentially made of hydrofluoroether as an immersion medium for immersing an immersion objective in light microscopy.

The present invention further relates to a cryo-light microscope comprising an immersion objective, a sample holder, and a cold stage carrying the sample holder. The cold stage comprises a metal base, the sample holder being connected to an end face of the metal base, a thermal insulation surrounding the end face of the, an immersion fluid reservoir radially extending between the sample holder and the thermal insulation, and having a circular opening surrounding the sample holder at the end face, and an immersion fluid supply channel extending through the thermal insulation.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 1A is a schematic cross section of an immersion objective with the front lens mount made amendment of a machinable glass ceramic, Macor®, operating as a thermal shield. The heat flows across sample, cover glass, immersion fluid, front lens, and ceramic mount. The low thermal expansion coefficient of the machinable ceramic allows reducing the thermal stresses. The high thermal resistance of Macor® allows confining most of the temperature gradient in the front lens mount as shown in the diagram. FIG. 1B shows the cold stage used for the implementation of cryo-immersion microscopy was designed to keep both sample and cryo-immersion fluid at a stable temperature by combining heating and temperature sensing. The stage is composed of two parts, a bottom copper bar, which is in direct contact with liquid nitrogen, and a top anodized aluminum post. The sample is placed on top of the aluminum post and in contact with the metal, below a cover slip. Cover slip and sample are secured magnetically to the post by using an iron gasket and a magnet glued inside the aluminum post. The immersion fluid is supplied to the reservoir through a channel in the PTFE. The opening in the PTFE allows forming a cold drop around the sample.

FIG. 3A shows room temperature (left) and cryogenic (right) wide field fluorescence images of *Escherichia coli* expressing GFP. FIG. 3B shows photobleaching curves for GFP expressed in *E. coli*. The red curve shows decay at room temperature and blue curve show decay at −140° C. In cryo-condition the GFP bleaching is suppressed about 3.5 times. FIG. 3C shows room temperature (left) and cryogenic (right) wide field fluorescence images of yeast cells expressing GFP tagged Pil1. FIG. 3D shows photobleaching curves for GFP expressed in yeast cells. The red curve shows decay at room temperature and blue curve show decay at −140° C. In cryo-condition the GFP bleaching is suppressed about 64 times. FIG. 3E shows a three-color wide field cryo-fluorescence image of plunge frozen U2OS cells labeled with AlexaFluor488 (vimentin cytoskeleton), AlexaFluor594 (Tom20 mitochondrial protein), and DAPI (cell nuclei).

FIG. 4A shows lateral and axial PSF acquired at −140° C. with the cryo-immersion objective and HFE-7200 immersion fluid. The intensity is normalized and shown on a logarithmic scale. FIG. 4B shows a simulated axial PSF for n=1.334. FIG. 4C shows lateral and axial PSF acquired at −130° C. with the cryo-immersion objective and HFE-7200 immersion fluid. FIG. 4D shows a simulated axial PSF for n=1.329. FIG. 4E shows lateral and axial PSF acquired at −90° C. with the cryo-immersion objective and HFE-7200 immersion fluid. FIG. 4F shows a simulated axial PSF for n=1.329. FIG. 4G shows lateral and axial PSF acquired at room temperature with the cryo-immersion objective and 6% Glycerol (n=1.337) as immersion fluid. FIG. 4H shows a simulated axial PSF for n=1.337.

DETAILED DESCRIPTION

Figure 1A:
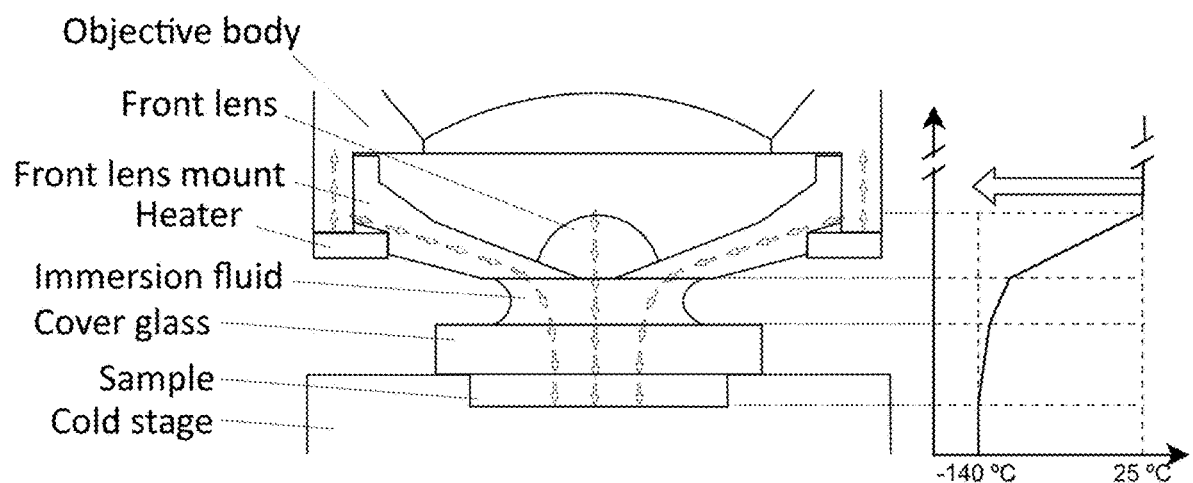
FIGS. 1A and 1B show details of an embodiment of the cryo-light microscope according to the present invention.

In one aspect, the present invention provides a new cryo-immersion medium essentially made of hydrofluoroether (HFE), which matches the refractive index of room-temperature liquid water and of cryo-temperature amorphous water.

The cryo-immersion medium according to the invention is a product including an immersion medium and an indication that the immersion medium is provided for immersing an immersion objective in light microscopy, the immersion medium being essentially made of hydrofluoroether The indication that the immersion medium is provided for immersing an immersion objective in light microscopy may particularly be implemented in instructions of use supplied with the immersion medium or on a container holding the immersion medium.

The HFE may particularly be selected from ethoxy-nonafluorobutane ($C_4F_9OC_2H_5$) and methoxy-nonafluorobutane ($C_4F_9OCH_3$). If the HFE is ethoxy-nonafluorobutane ($C_4F_9OC_2H_5$), it may be made of $(CF_3)_2CFCF_2OC_2H_5$ (CAS No. 163702-06-5) and/or $CF_3CF_2CF_2CF_2OC_2H_5$ (CAS No. 163702-05-4).

HFE-7200 or 3M™ Novec™ 7200 Engineered Fluid, see http://multimedia.3 m.com/mws/media/199819O/3mtm-novectm-7200-engineered-fluid.pdf is a suitable immersion fluid according to the present invention. It consists of ethoxy-nonafluorobutane ($C_4F_9OC_2H_5$), or more particularly of one or both of the inseparable isomers $(CF_3)_2CFCF_2OC_2H_5$ (CAS No. 163702-06-5) and $CF_3CF_2CF_2CF_2OC_2H_5$ (CAS No. 163702-05-4) which display essentially identical properties. In the following, HFE-7200 refers to ethoxy-nonafluorobutane ($C_4F_9OC_2H_5$) as defined in this paragraph.

At about −140° C. HFE-7200 has a refractive index which is essentially the same as the refractive index of water at room temperature. Thus, HFE-7200 may be used as an immersion medium with commercial water immersion objectives for cryo-light microscopy.

HFE-7100 or 3M™ Novec™ 7100 Engineered Fluid, see http://multimedia.3 m.com/mws/media/199819O/3mtm-novectm-7200-engineered-fluid.pdf is another suitable immersion fluid according to the present invention.

Mixtures of one or more HFE, or mixtures of one or more HFE with other substances at low concentration, given that these mixtures still satisfy the criteria of index-matching, are also suitable immersion fluids according to the present invention. Examples of such mixtures may include one or more HFE with other perfluorocarbons, common solvents, or cryogenic liquids, including 2-methylbutane (isopentane), propane, ethane, methyl cyclohexane, cyclohexane, methyl cyclopentane. As a rule, the non-HFE content of the immersion medium according to the present invention is not higher than 33% by volume; typically it is not higher than 20% by volume; most times it is not higher than 10% by volume; often it is not higher than 3% by volume; and it may be so close to zero that the immersion medium may be regarded as pure HFE.

In another aspect, the present invention provides a new technological concept for a cryo-light microscope in which the body of the objective and the front lens are not in thermal equilibrium. This concept includes providing a heat flow from a front lens mount through an immersion medium contacting the front lens towards a sample to be imaged. Thus, the immersion medium, particularly when using a glass cover on the sample, even in its parts which are closest to the sample, is on a temperature which is at least slightly higher that the sample. As a result, the sample may even be kept at or slightly below a freeze point of the immersion medium without freezing the liquid immersion medium. Generally, the new technological concept for a cryo-light microscope is applicable down to a cryogenic temperature of, for example, −196° C. Such a low sample temperature may, however, require some fine tuning with regard to the working distance of the immersion objective and the composition of immersion medium.

Without any fine tuning and simply using the above indicated HFE immersion media of the present invention, the sample to be imaged may be kept at a cryogenic temperature in a range from −130° C. to −145° C. The heat flow is coupled into the immersion fluid at the front lens mount for the front lens of the immersion objective. A backside of the front lens may be purged with dry nitrogen. The heat flow may be directed into a cold stage carrying the sample holder.

A cryo-light microscope according to the present invention comprises an immersion objective, a sample holder and a cold stage carrying the sample holder, the cold stage having a metal base preferably made of aluminum, the sample holder being connected to an end face of the metal base, a thermal insulation surrounding the end face of the metal base, an immersion fluid reservoir radially extending between the sample holder and the thermal insulation, and having a circular opening surrounding the sample holder at the end face, and an immersion fluid supply channel extending through the thermal insulation.

The temperature sensor and a stage heating device may be connected to the metal base, the stage heating device being farther away from the end face than the temperature sensor.

It could be shown that the present invention can provide superior contrast in *E. coli* and yeast cells expressing fluorescent proteins and resolve sub-micrometer structures in multi-color immunolabeled human bone osteosarcoma epithelial (U2OS) cells at −140° C.

This temperature and all other temperatures indicated here are actually those of the temperature sensor located at the metal base preferably made of aluminum. Thus, they are the temperatures of the sample attached to the highly thermally conductive metal part but not exactly the temperatures even of the coldest part of the immersion medium arranged between the sample and the immersion objective.

The immersion medium being liquid will also be called the immersion fluid here.

The present disclosure also relates to a cryo-light microscope comprising an immersion objective including an objective body, an immersion objective, a front lens mount connected with the objective body at its outer circumference and holding the front lens at its center, and a heating device, a sample holder, and a cold stage carrying the sample holder. The heating device couples a heat flow into the front lens mount near its connection with the objective body.

The front lens mount may comprise a flange which holds the front lens and covers a part of the front lens at its center and into which the heat flow is coupled by the heating device at its outer circumference. The flange, in an area around the uncovered part of the objective lens, is will be immersed in an immersion medium in operation of the cryo-light microscope. The flange is made of a material having a thermal expansion coefficient of not more than $10^{-5}$ m/(m·K) and a thermal conductivity of not more than 10 W/(m·K). Particularly, the material of the flange may be selected from a ceramic, a machinable ceramic, a glass ceramic, a machinable glass ceramic, a polymer and a polyamide-imide. A suitable ceramic is Macor®, and a suitable polymer is Torlon®.

In this cryo-light microscope according to the present disclosure, the heating device is connected to both the front lens mount and the objective body made of metal.

Figure 1B:
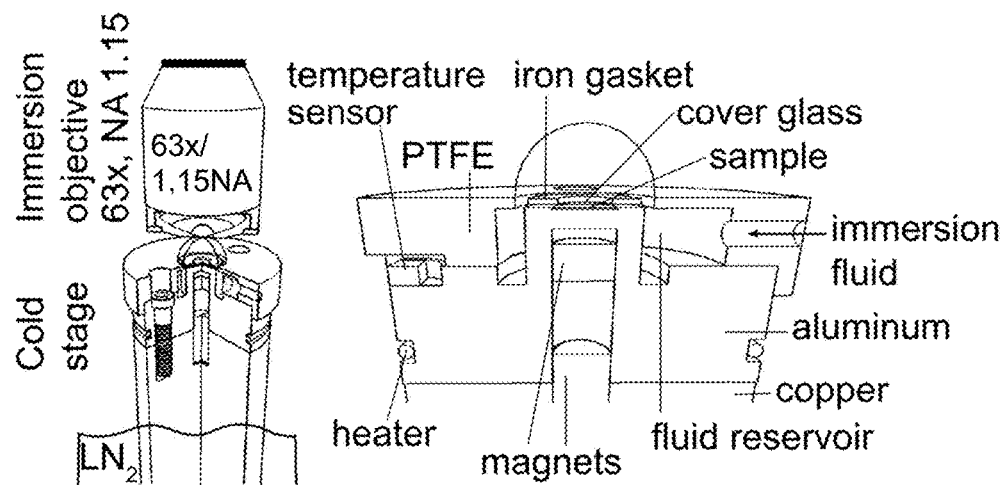

Referring now in greater detail to the drawings, the present invention is a new approach towards immersion light microscopy at −140° C. In the present invention, the new immersion medium, HFE-7200, which matches the refractive index of room-temperature water at cryogenic temperature with the new technological concept in which the objective itself is not in thermal equilibrium. The temperature drop is maintained by actively heating the ceramic lens mount along the perimeter near its connection with the objective body (see FIGS. 1A and 1 B). An important advantage of this approach is that refractive index gradients due to temperature variations in the liquid are small and not likely to distort the wavefront.

To implement this approach, the inventors prototyped a cryo-immersion objective starting from a commercial water immersion bio-imaging objective (Zeiss LD C-Apochromat 63×, NA=1.15). The inventors chose this objective mainly for (I) its long working distance (600 μm), which helps to minimize heat transfer to the sample, and (II) the built-in correction collar, which can be used to correct residual spherical aberration. To prevent condensation and frost build-up, the interior of the objective is purged continuously with dry nitrogen gas. This is made possible by custom-integrated channels, which traverse the objective body and end with holes in the front lens mount made of machinable glass ceramic. To maintain the objective at 25° C., all heat losses are compensated by an electrically heated copper ring attached near the transition between the ceramic front lens mount and the metallic housing of the objective.

Searching for a suitable immersion medium, the inventors found that the partially fluorinated liquid ethoxy-nonafluorobutane (HFE-7200), has a surprisingly low refractive index (1.28) at room temperature and a liquid range from >70° C. to below −140° C. Note that HFE-7200 is also inexpensive, non-toxic, and safe for the environment.

Figure 2A:
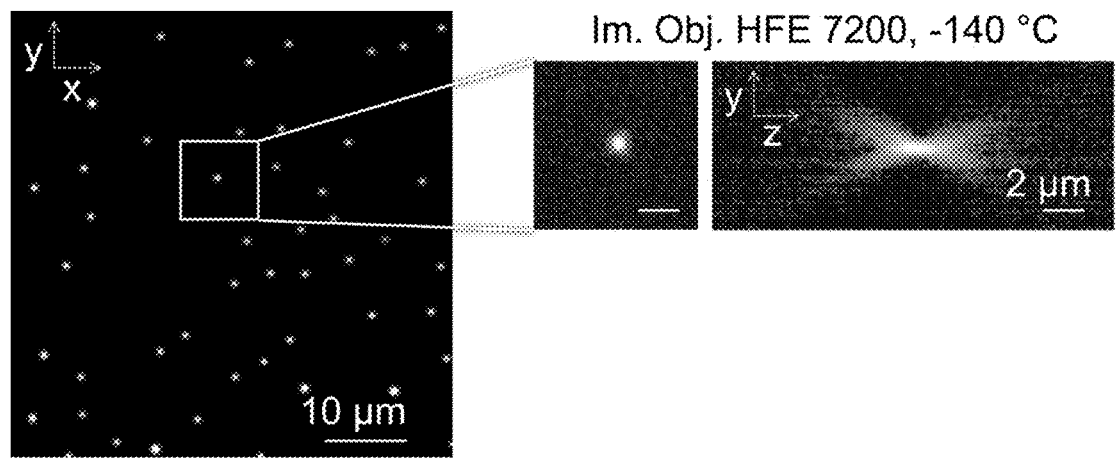
FIG. 2A shows lateral and axial PSF measured at −140° C. with the cryo-immersion objective for the immersion fluid HFE-7200. Fitting the PSF to a two dimensional Gaussian (not shown) allows to determine lateral and axial resolution. The intensity is normalized and shown on a logarithmic scale.

Combining the new cryo-immersion objective with the optical properties of HFE-7200, the inventors were able to perform fluorescence cryomicroscopy free from spherical aberrations at −140° C. (FIG. 2A).

Figure 2B:
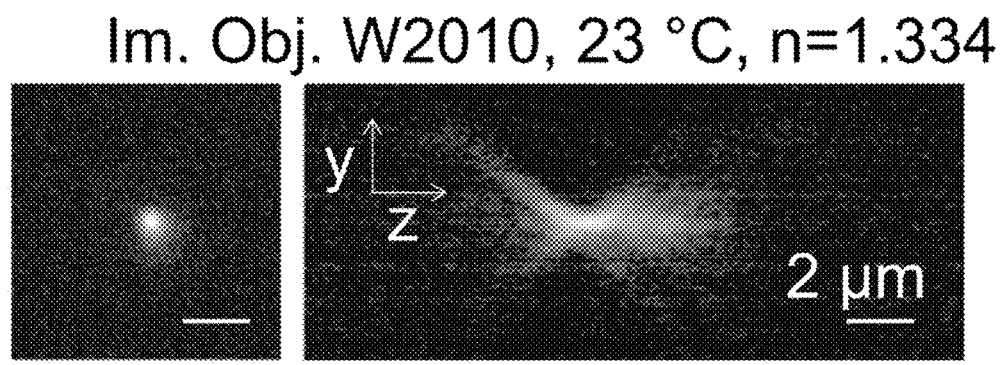
FIG. 2B shows lateral and axial PSF measured at room temperature with the cryo-immersion objective for the commercial immersion fluid W2010.

To find the optimal working temperature, the inventors compared the point spread function (PSF) of their objective with HFE-7200 immersion to the PSF at room temperature using the standard medium (Zeiss W2010, n=1.334) (FIG. 2B). As a reference, the inventors also compared the results with the performance of an air objective (Zeiss LD Achroplan 63×/0.75, working distance 2.8 mm) in cryo-conditions and at room temperature (see FIG. 2E and FIG. 2F and Table 1).

One of the key advantages of immersion objectives over air objectives is their light collection efficiency, which grows as ~$NA^2$. Indeed the inventors measured an increase in brightness of 5.7±0.6 times from a 63×/0.75 air objective to the 63×/1.15 immersion objective according to the present invention at −140° C. This is in agreement with the expected scale factor of ~$NA^4$ for widefield fluorescence imaging.

As a demonstration of possible applications of the present invention, the inventors imaged *Escherichia coli* cells expressing green fluorescent protein (GFP), yeast cells expressing GFP-tagged Pil1, and immunostained human bone osteosarcoma epithelial cells (U2OS) (see FIGS. 3A to 3E). *E. coli* and yeast cells were imaged in both live ambient conditions and after plunge freezing in cryo-condition.

Figure 3A:
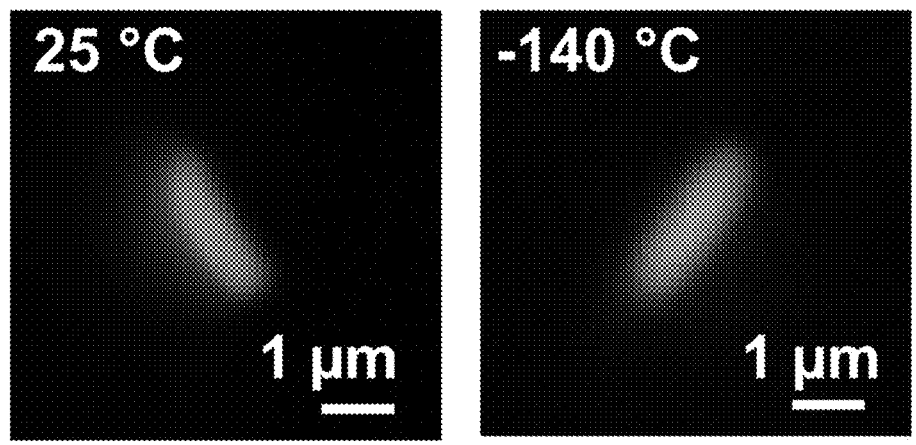
FIGS. 3A to 3E illustrate imaging of cryofixed biological specimens with the prototyped to cryo-immersion objective.
Figure 3B:
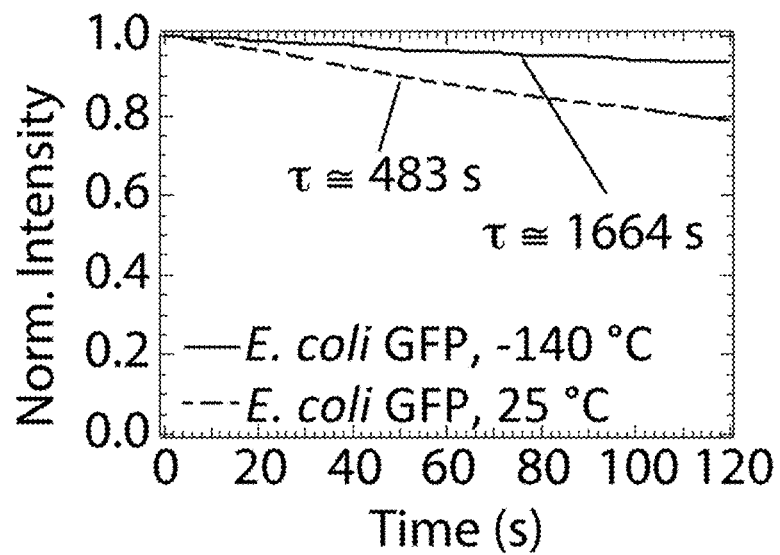
Figure 3C:
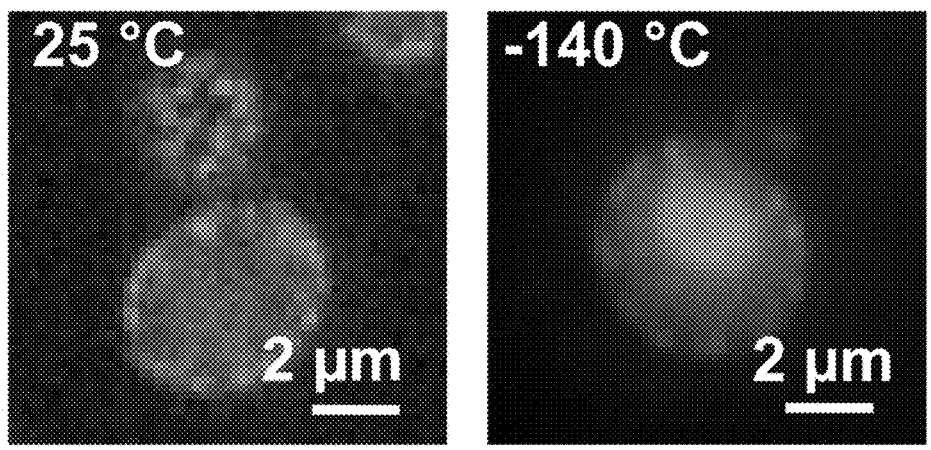
Figure 3D:
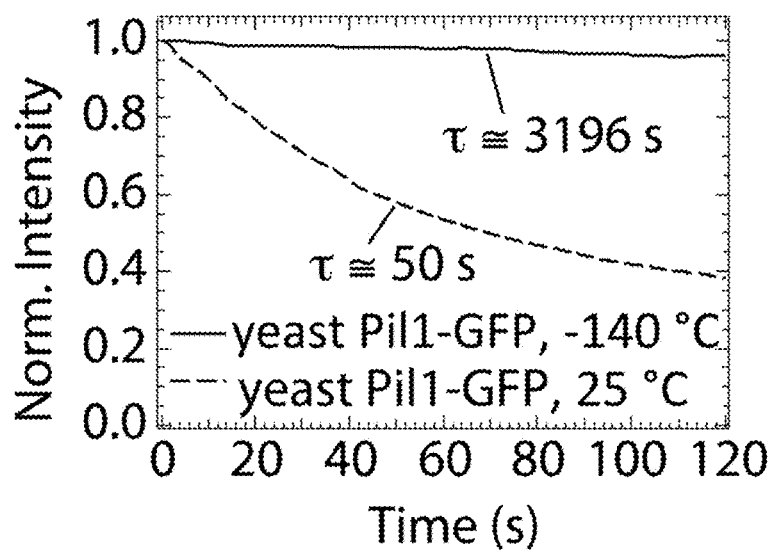
Figure 3E:
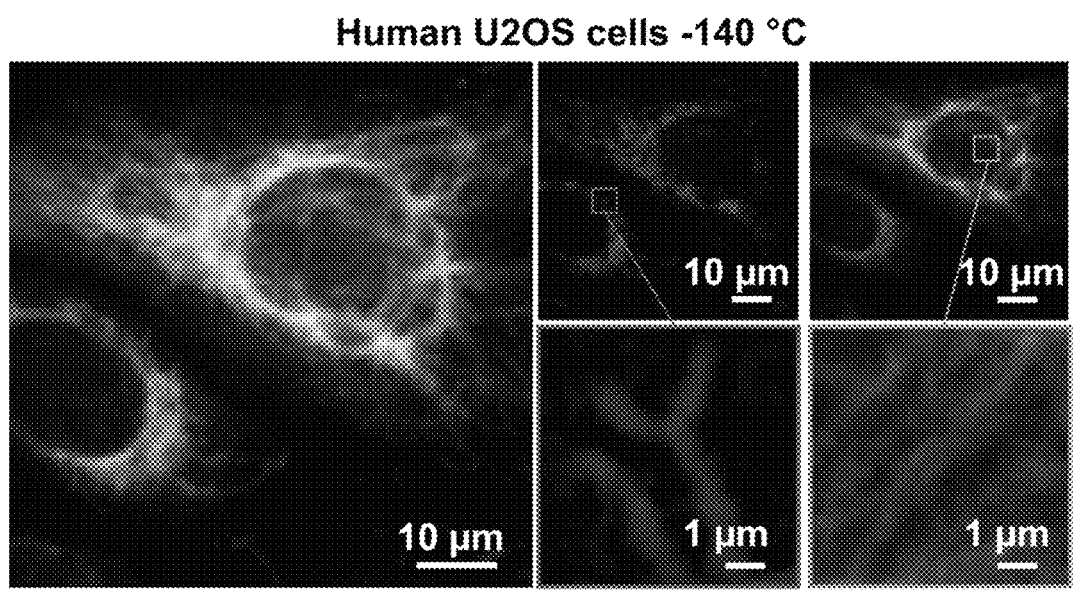

The benefits of cryo-fixation and imaging in cryo-conditions are particularly evident for yeast cells (FIG. 3C). A considerable improvement of both signal-to-noise ratio and image quality is achieved in cryo-conditions where the photobleaching is suppressed around 64 times (FIG. 3D). In the cryofixed cells, a fluorescence signal also appears at locations that are dark at room temperature. This can be due to an increase in the auto-fluorescence of some specific biomolecules at low temperature or due to alterations introduced during sample preparation and plunge freezing. No particular structural differences are appreciable in images of live *E. coli* and cryofixed *E. coli* (FIG. 3A). GFP expressed in bacteria bleaches relatively slowly already at room temperature, and the rate is suppressed only by a factor of 3.5 in cryo-conditions (FIG. 3B). Further, the inventors established the possibility of resolving sub-micrometer cell structures by multicolor cryo-fluorescence microscopy using the present invention. FIG. 3E illustrates the attainable image quality in widefield fluorescence of immunostained U2OS cells at −140° C. Networks of mitochondria (Tom20 immunolabeled with AlexaFluor594-decorated antibodies) and vimentin filaments (AlexaFluor488) are well resolved simultaneously. This surprising finding indicates that the

TABLE 1

FWHM of the PSF measured in cryo-condition (−140° C.) and at room temperature using the prototyped cryo-immersion objective (63 ×/1.15) and comparison with an air objective (63 ×/0.75).

|  | FWHMxy (nm) | FWHMz (nm) | Peak intensity (a.u.) |
| --- | --- | --- | --- |
| Cryo-Im. Obj W2010 @ 23° C. | 295 ± 6 | 902 ± 17 | 8444 ± 484 |
| Cryo-Im. Obj HFE 7200 @ −140° C. | 353 ± 16 | 1554 ± 58 | 3449 ± 362 |
| Air Obj. 0.75 NA @ −140° C. | 385 ± 14 | 1743 ± 108 | 610 ± 165 |

The overall shape and symmetry of the PSFs are very similar at −140° C. (HFE-7200) and at 23° C. (Zeiss W2010), indicating that the refractive index of HFE-7200 is well matched to the design of the objective at this temperature. Importantly, the PSFs were very uniform across the entire field of view (see 2D heat maps in FIGS. 2A to 2H), which is critical in widefield and beam scanning microscopy techniques. The symmetry of the PSFs and their uniformity over the field indicate that there are no significant lateral refractive index gradients in the medium.

Figure 2C:
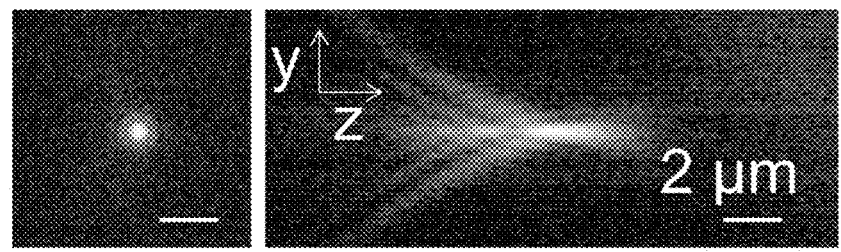
FIG. 2C shows lateral and axial PSF measured at room temperature with the cryo-immersion objective for 6% Glycerol (n=1.337) as immersion fluid. The refractive index mismatching produces positive aberrations.
Figure 2D:
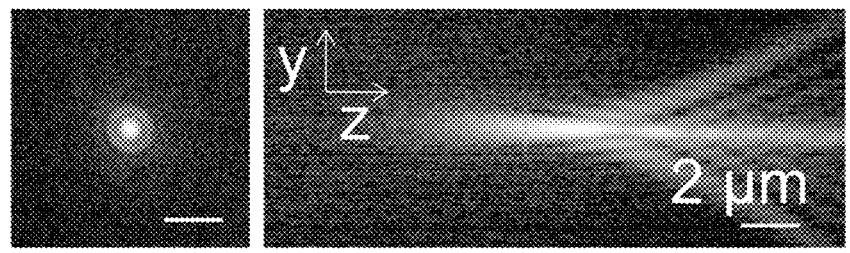
FIG. 2D shows lateral and axial PSF measured at −90° C. with the cryo-immersion objective for the immersion fluid HFE-7200. The refractive index of the immersion fluid at −90° C. is smaller than the refractive index of water at room temperature, producing negative aberrations.
Figure 2E:
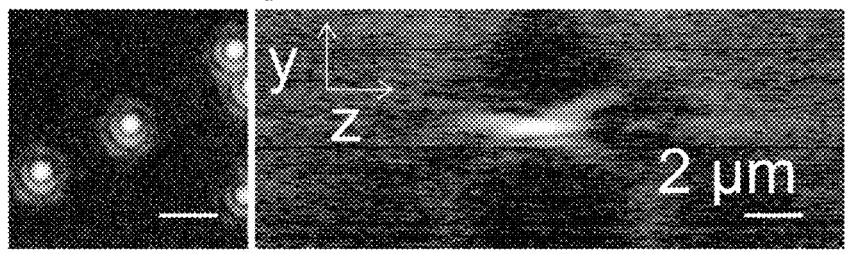
FIG. 2E shows lateral and axial PSF measured at −140° C. with the 0.75 NA air objective.
Figure 2F:
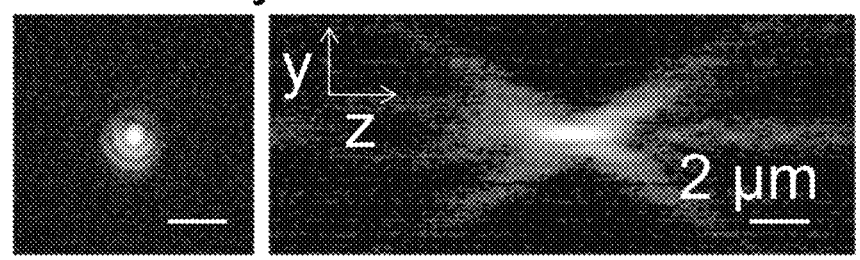
FIG. 2F shows lateral and axial PSF measured at room temperature with the air objective.
Figure 2G:
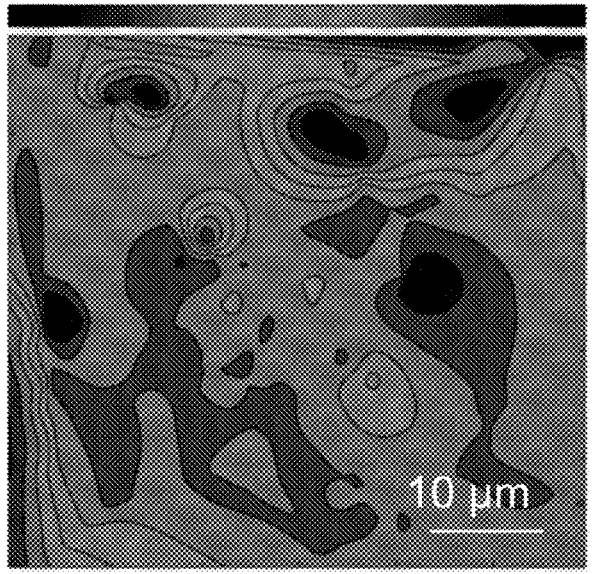
FIG. 2G is a 2D heat map of the measured lateral FWHM at −140° C.
Figure 2H:
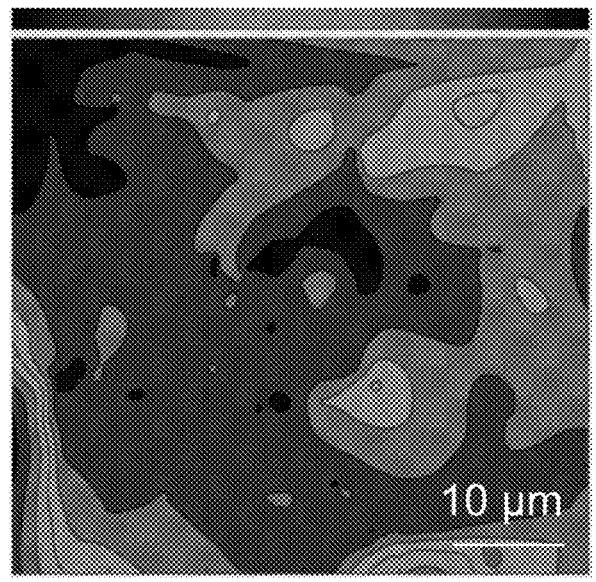
FIG. 2H is a 2D heat map of the measured axial FWHM at −140° C.
Figure 4A:
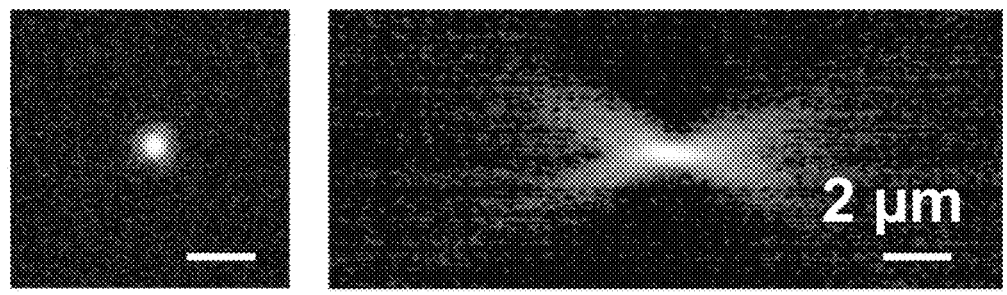
FIGS. 4A to 4H compare measured PSFs with PSFs simulated with PSFLab for a water objective with NA=1.15.26 The distance from the glass slide was set to 0 and the refractive indexes over and below the glass slides were set to the value reported in the figures.
Figure 4B:
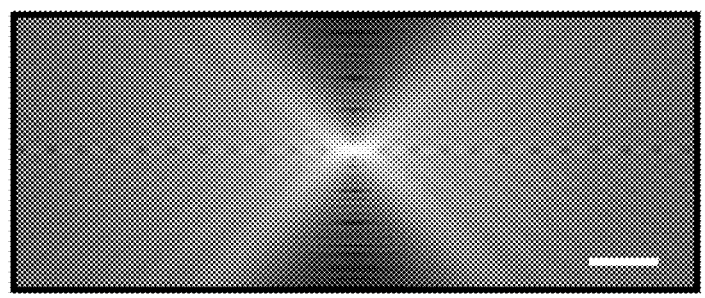
Figure 4C:
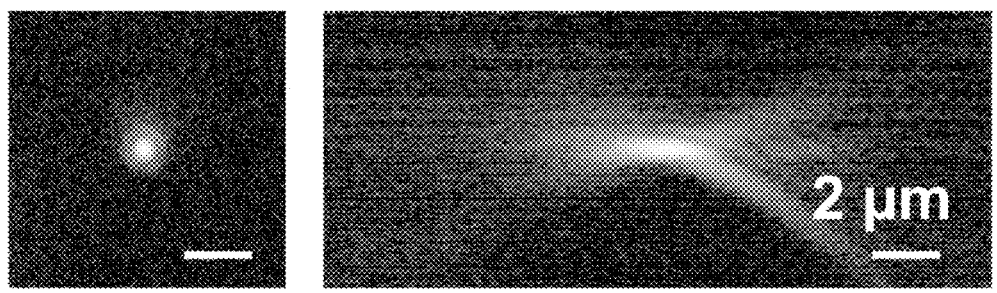
Figure 4D:
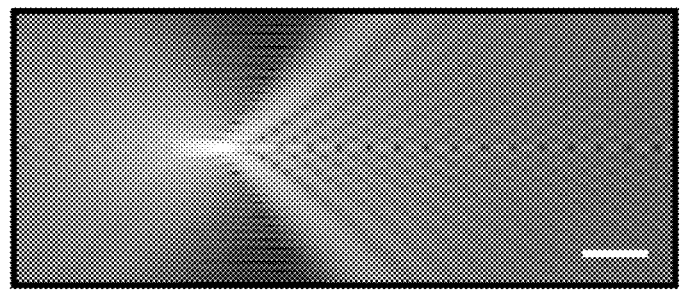
Figure 4E:
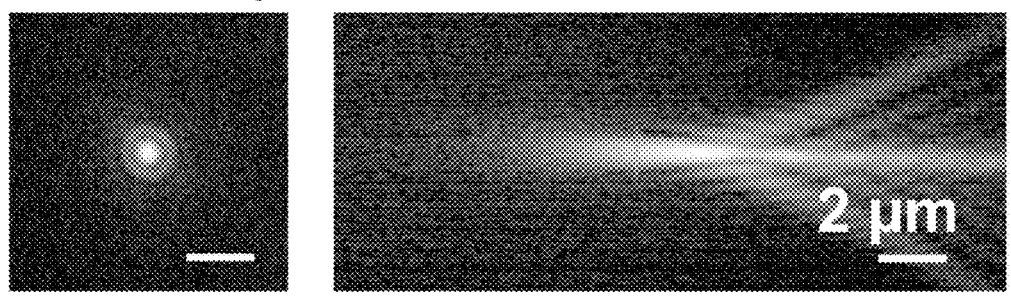
Figure 4F:
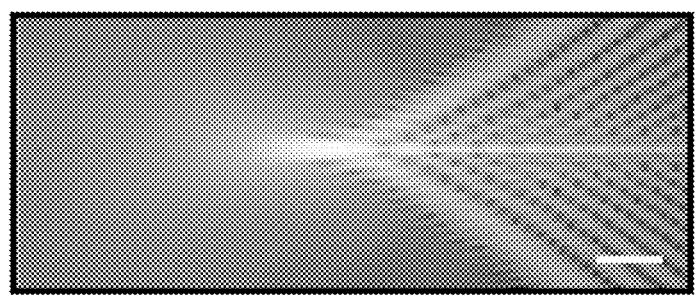
Figure 4G:
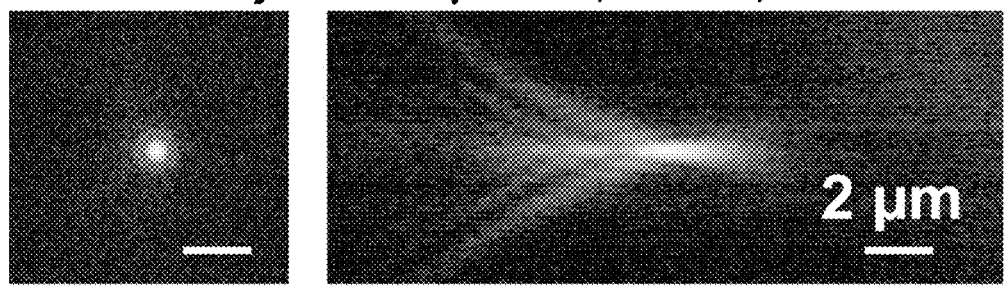
Figure 4H:
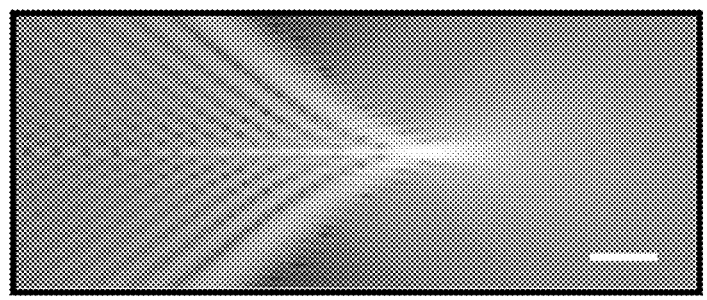

To assess the level of index matching more quantitatively, the inventors conducted various measurements of the PSF with purposely mismatched conditions. At room temperature, using a 6% glycerol solution (n=1.337) produces significant positive spherical aberration, as seen in FIG. 2C. In cryo-conditions, the inventors observed increasing negative spherical aberration when the temperature was raised from −140° C. over −130° C. (FIGS. 4A and 4C) to −90° C. (FIG. 2D).

dispersion of HFE-7200 must also be close to the design of the objective. However, more detailed measurements will be needed to assess lateral and axial chromatic aberrations quantitatively.

In conclusion, the inventors demonstrated a new concept to approach diffraction-limited performance in high-NA cryo-fluorescence microscopy with commercially available immersion objectives. To achieve this, the inventors created a thermally shielded microenvironment around the sample by replacing the metallic front lens mount of the objective with an insulating ceramic mount that is heated around its perimeter. A further enabling step was the finding of an immersion medium, HFE-7200, that provides accurate index matching at a sample temperature below the glass transition of water. Surprising is that although the front lens of the objective is made from two separate elements bonded by an adhesive, the inventors have not observed any damage throughout hundreds of hours of use. The bond between the front lens and the ceramic lens mount also remained stable. This is likely the case because all glued components have very similar thermal expansion coefficients and are only a few millimeters in size.

Some limitations remain to be addressed. Firstly, the objective used by the inventors only provides a numerical aperture of 1.15. While it may be expected that the concept of the present invention of thermally isolating the front lens will also work for oil objectives with NA>1.4, new immersion media would then need to be identified. This is likely feasible, as numerous non-toxic fluids with a wide liquid range and a higher refractive index than HFE-7200 exist.

Secondly, the axial PSF at low temperature is ~1.7 times wider than at room temperature. In part, this may be due to a combination of stage drift and vibration, which are both significant in the current system. Another factor can be the presence of a small axial temperature gradient throughout the immersion medium. This is unavoidable since the cryo-light microscope according to the present invention inherently operates away from thermal equilibrium. However, the temperature drop can still be reduced by lowering the temperature of the objective body or by further increasing the thermal resistance of the lens mount. Importantly, there is evidence that the continuous heat transfer through the objective still does not warm the sample significantly. A large temperature increase would be measurable as an unexpected increase in the intensity of the fluorescent beads used in the PSF characterization when imaging in immersion. This, however, is not observed.

The present invention will enable the combination of advanced light microscopy, including TIRF or STED, with electron cryo-light microscopy in order to help elucidate connections between structure and function at the sub-cellular and molecular scale.

Methods

Sample Preparation

Fluorescent Nanobeads Deposition

Fluorescent beads of diameter ø=175 nm and emission peak wavelength $\lambda_{em}$=525 nm (Merck Millipore, Estapor®) were deposited on the surface of circular #1.5 coverslips 5 mm in diameter (Engelbrecht GmbH, Edermünde, Germany). The coverslips were plasma cleaned, incubated for 5 min in 1% poly-L-lysine (Sigma-Aldrich, St. Louis, Mo., USA), rinsed with DI water, and then covered with 25 µl of beads solution (3.4×108 pt/ml). The particle suspension was left to dry for 2 hours in a vacuum chamber.

E. coli Cells Preparation

For protein expression, the plasmid pQE-31-GFP were transferred into E. coli expression strain BL21-CP-RIL. The bacteria were cultured in LB medium agar plates. Fluorescent colonies were selected and further cultured in liquid LB medium. The growth medium was replaced with DI water before ambient condition live imaging or plunge freezing on Formvar/Carbonkely the case because all glued components have very coated TEM grids (Plano GmbH). Grids were blotted and plunged in liquid nitrogen-cooled propane using a homemade freezing device. Samples were stored in submerged in liquid nitrogen for later imaging.

Yeast Cells Preparation

Yeast cells expressing Pil1-GFP were cultured in liquid YPD medium. The growth medium was replaced with DI water before ambient conditions imaging or plunge freezing. Room temperature microscopy was performed after fixing yeast cells on poly-L-lysine (Sigma-Aldrich, St. Louis, Mo., USA) coated coverslips. For the preparation of samples for cryomicroscopy, were used poly-L-lysine covered sapphire discs, 3 mm diameter, 50 µm thick (Engineering Office M. Wohlwend GmbH, Sennwald, Switzerland). The cells were vitrified by plunge freezing in liquid nitrogen-cooled propane. Water in excess was removed with filter paper. Samples were stored submerged in liquid nitrogen for later imaging.

U2OS Cells Preparation

Human U2OS cells were cultured in DMEM, high glucose, GlutaMAX medium (Thermo Fisher Scientific, Waltham, Mass., USA) supplemented with 100 U/ml penicillin and 100 µg/ml streptomycin (Merck Millipore, Darmstadt, Germany), 1 mM sodium pyruvate (Sigma-Aldrich, St. Louis, Mo., USA), and 10% (v/v) fetal bovine serum (Merck Millipore) at 37° C. and 5% $CO_2$. Cells were seeded on sapphire crystal discs (Engineering Office M. Wohlwend GmbH, Sennwald, Switzerland) and grown overnight. Cells were fixed with pre-warmed 4 formaldehyde in PBS (137 mM NaCl, 2.68 mM KCl, 10 mM Na2HPO4, pH 7.4) for 10 minutes at 37° C., extracted with 0.5% (v/v) Triton-X-100 in PBS, blocked with 5% (w/v) bovine serum albumin in PBS and incubated with polyclonal antibodies against the mitochondrial protein Tom20 (Santa Cruz Biotechnology, Santa Cruz, Calif., USA) and vimentin (Sigma-Aldrich) for 1 h. After five washing steps with PBS and blocking with 10% (w/v) BSA in PBS, primary antibodies were detected with secondary sheep-anti-mouse Alexa Fluor 488 antibodies (Invitrogen, Carlsbad, Calif., USA) or goat-anti-rabbit-antibodies (Jackson ImmunoResearch Laboratories, West Grove, Pa., USA) custom-labeled with Alexa Fluor 594 (Life Technologies) for 1 h. Samples were washed five times with PBS and covered with PBS containing 2.5 µg/ml DAPI (Sigma-Aldrich). The cells were vitrified by plunge freezing in liquid nitrogen-cooled propane. Samples were stored submerged in liquid nitrogen for later imaging.

Optical Setup and Image Acquisition

Figure 5A:
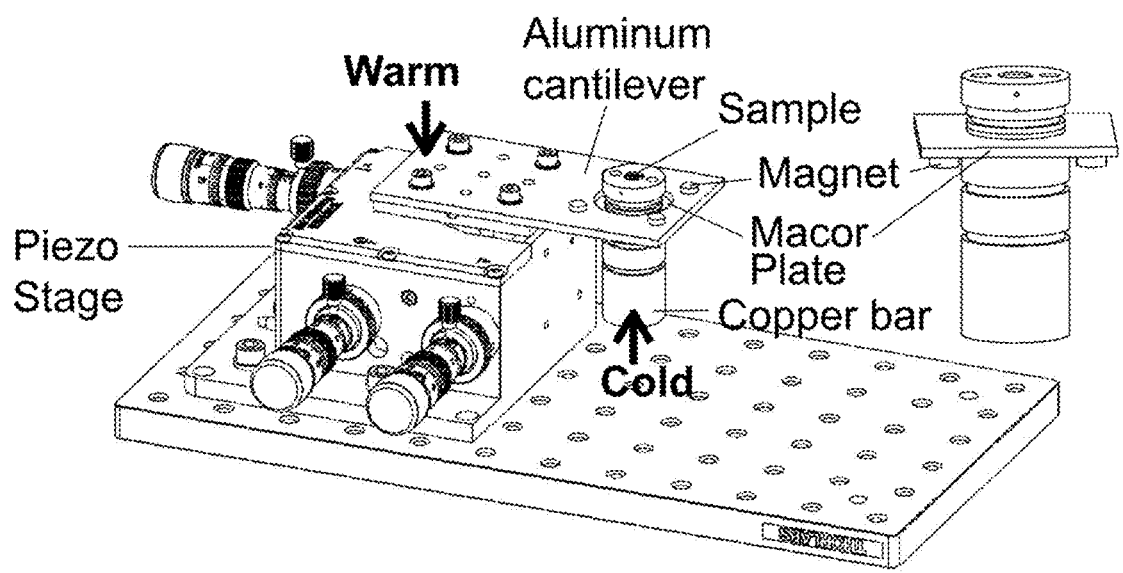
FIGS. 5A and 5B show further details of a cryo-stage of the cryo-light microscope according to FIGS. 1A and 1B.
Figure 5B:
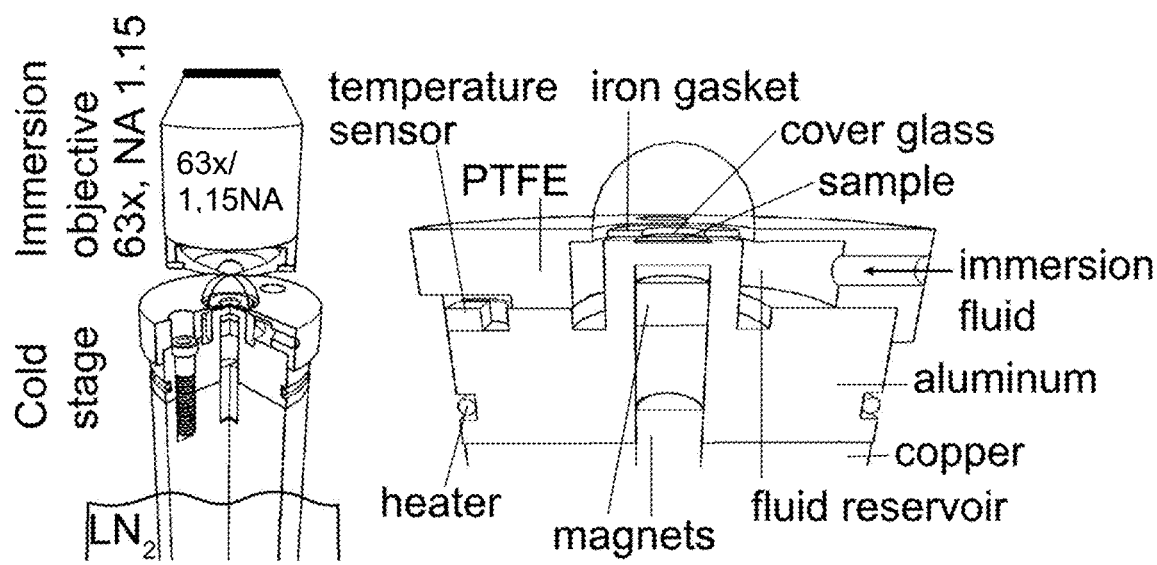

All experiments were performed with an upright microscope (ZEISS Axio Scope.A1) equipped with a compact mercury light source (HXP 120, LEJ). The mechanical stage of the microscope was replaced with a piezo stage (3-Axis NanoMax Stage, Thorlabs) mounted on a 30×15 cm breadboard (see FIG. 5A). The breadboard is fixed to the microscope stage carrier. In this configuration, the stage can move in the x, y, and z axis with a span of 4 mm. The piezo is used to drive the movement of the stage in the z axis only during imaging. Axial movements during objective approach and focusing are performed using the focusing drive of the microscope. Both piezo stage and camera were controlled by µManager.[22]

To minimize accumulation of frost, the stage is surrounded by an acrylic glove box designed to seal around the microscope objectives turret. Nitrogen gas is flushed inside the box in order to maintain humidity levels of less than 10% during operation in cryo-conditions.

The cold stage, consisting of a metal bar, is hold suspended inside a liquid nitrogen container serving as a heat sink. A plate made of machinable glass ceramic and glued around the copper bar is used to fix magnetically the bar to a rigid aluminum cantilever moved by the piezo stage. This configuration allows minimizing the vibration transferred to the stage by the boiling liquid nitrogen and, at the same time, to minimize the heat transfer to the piezo stage and thus keep cold only the metal bar.

The metal bar supporting the specimens consists of a bottom part in copper and a top part in anodized aluminum. A graphite sheet 130 µm thick is placed in between the two parts in order to maximize the thermal gradient at the junction. The temperature of the top part is controlled using a PT100 sensor and a NiCr heater. A temperature up to −90° C. can be kept stable by applying a maximum power of 30 W to the heater.

The specimen is placed in direct contact with the anodized aluminum protruding post. A recess (diameter 3.2 mm, depth 100 μm) allows to place TEM grids and 50 μm thick sapphire discs below the cover glass and avoid to damage the biological specimens. Importantly, when imaging biological specimens on TEM grids and sapphire discs the space between sample carrier and coverglass is filled with cryo-immersion fluid. The sample is secured to the stage using magnetic fixing of an iron gasket placed on top of the coverglass. For this propose a magnet is glued inside the aluminum bar below the sample. The cryofixed samples are transferred from liquid nitrogen to the stage inside the dry box just before imaging. During the transfer, the temperature of the stage was kept at around −180° C. After securing the sample to the stage the temperature is raised to −150° C. and the immersion fluid is supplied into a reservoir opened in between a PTFE cup and the aluminum top bar after being pre-cooled to −90° C. The liquid is cooled to the stage temperature while flowing inside a needle inserted in the PTFE and in contact with the metal stage. The opening of the cup around the post supporting the specimen makes possible to form a liquid cold drop on top of the sample and to contact the cryo-objective.

The air objective (Zeiss LD Achroplan 63×, NA=0.75, working distance 2.8 mm) and the cryo-immersion objective (Macon® front lens mount-Zeiss LD C-Apochromat 63×, NA=1.15) are both mounted on the microscope turret during operation. The cryo-immersion objective is mounted on a specifically designed trade adapter sealed with a fused silica tilted window and equipped with an inlet tube that allows flushing nitrogen gas through the cryo-objective body. The nitrogen gas exit the objective from holes in the front lens mount of the objective. The objective body temperature is kept at 25° C. by controlling the temperature of a heater ring mounted at the connection between the ceramic front lens mount and the metal objective body. Before imaging, the stage is raised slowly to put the front lens objective in contact with the immersion fluid. When imaging cryofixed biological samples the stage temperature is kept at −150° C. during the approaching phase. After around 10-15 min, time estimated being enough for the front lens to cool down, the temperature of the stage is raised to −140° C. and focusing is performed.

Point Spread Function Measurements

Fluorescent images of sub-resolution polystyrene beads of diameter ⌀=175 nm and emission peak wavelength $\lambda_{em}$=525 nm (Merck Millipore, Estapor®) were acquired using a front-illuminated CMOS camera with 2560×2160 6.48 μm pixels (Andor, Neo) mounted on a 2.5× beam expander and the filter set 38HE (Zeiss). Only 50% of the camera frame was used and the integration time was set to 200 ms for all measurements. Beads were sampled at 200 nm steps along the z axis. PSFs were measured at room temperature for W2010 immersion fluid and 6% glycerol. In cryo-conditions, the PSFs were measured for HFE 7200 at temperatures ranging between −90° C. and −140° C. with a step of 10° C. PSFs for air were measured with the air objective (Zeiss LD Achroplan 63×, NA=0.75, working distance 2.8 mm).

PSFs were measured on the same sample spot for comparing the intensity values. The following method was followed: (i) Imaging with air objective in ambient conditions; (ii) Cooling of the stage and imaging with air objective in cryo-conditions; (iii) Injection of HFE-7200 in the stage and imaging with the cryo-immersion objective in cryo-conditions; (iv) Heating to room temperature of the stage and imaging with cryo-immersion objective with W2010 immersion fluid. HFE 7200 evaporates without leaving traces in few minutes once the stage reach room temperature allowing to put W2010 on top of the sample and to perform imaging at room temperature. Image processing and analysis were carried out using Fiji.[23] FWHM values were measured using the plugin GDSC SMLN after running an inverted deconvolution run for correcting for finite size of the beads using the plugin Deconvolutionlab2.[24]

Imaging of E. coli and Yeast Cells

Fluorescent images of E. coli and yeast cells were acquired using a back-illuminated EMCCD with 512×512 16 μm pixels (Andor, IXON 987) mounted on a 2.5× beam expander, and the filter set 38HE (Zeiss). For E. coli the inventors used an integration time of 10 ms and EM gain 20. For yeast cells, the integration time was raised to 100 ms and the EM gain to 50.

Photobleaching assays were performed at room temperature and at −140° C. by continuously exposing the sample to the microscope lamp light. Images were recorded at 250 ms intervals for a total exposure time of 2 minutes. The inventors subtracted the average intensity of the background from the average intensity of the signal inside a boundary that contained the entire cell. For images of yeast cells in cryo-condition, this boundary was chosen to contain only the Pil1 spots. In order to correct for drifting the images were aligned using the Fiji plugin for the recursive alignment of a stack of images StakReg.[25] The inventors calculated the bleaching rate as the integral-tau of the decay curve defined as $\tau = \int R \cdot I(t) \, dt / \int R \, I(t) \, dt$.

Imaging of U2OS Cells

Fluorescent images of immunolabeled human U2OS cells were acquired using the wide field modality of the white light confocal microscopy system (Revolution DSD, Andor) equipped with a CCD camera 1262×1031 6.45 μm pixels (Clara, Andor) and filter set D/F/T (Dapi, FITC, Texas Red). The integration time was set to 2 s for the each channel. Image processing and analysis were carried out using Fiji.[23]

Advantageous developments of the invention result from the claims, the description and the drawings. The advantages of features and of combinations of a plurality of features mentioned at the beginning of the description only serve as examples and may be used alternatively or cumulatively without the necessity of embodiments according to the invention to having to obtain these advantages. Without changing the scope of protection as defined by the enclosed claims, the following applies with respect to the disclosure of the original application and the patent: further features may be taken from the drawings, in particular from the illustrated designs and the dimensions of a plurality of components with respect to one another as well as from their relative arrangement and their operative connection. The combination of features of different embodiments of the invention or of features of different claims independent of the chosen references of the claims is also possible, and it is motivated herewith. This also relates to features which are illustrated in separate drawings, or which are mentioned when describing them. These features may also be combined with features of different claims. Furthermore, it is possible that further embodiments of the invention do not have the features mentioned in the claims.

The number of the features mentioned in the claims and in the description is to be understood to cover this exact number and a greater number than the mentioned number without having to explicitly use the adverb "at least". For example, if an element is mentioned, this is to be understood such that there is exactly one element or there are two elements or more elements. Additional features may be added to these features, or these features may be the only features of the respective product.

Many variations and modifications may be made to the preferred embodiments of the invention without departing substantially from the spirit and principles of the invention. All such modifications and variations are intended to be included herein within the scope of the present invention, as defined by the following claims.

REFERENCES

1. Kaufmann, R., Hagen, C. & Grüunewald, K. Fluorescence cryo-microscopy: current challenges and prospects. Curr. Opin. Chem. Biol. 20, 86-91 (2014). URL http://www.sciencedirect.com/science/article/pii/S1367593114000623. DOI 10.1016/j.cbpa.2014.05.007.
2. Schwartz, C. L., Sarbash, V. I., Ataullakhanov, F. I., Mcintosh, J. R. & Nicastro, D. Cryo-fluorescence microscopy facilitates correlations between light and cryo-electron microscopy and reduces the rate of photobleaching. J. Microsc. 227, 98-109 (2007). DOI 10.1111/j.1365-2818.2007.01794.x.
3. Kaufmann, R. et al. Super-Resolution Microscopy Using Standard Fluorescent Proteins in Intact Cells under Cryo-Conditions. Nano Lett. 14, 4171-4175 (2014). URL http://pubs.acs.org/doi/abs/10.1021/nl501870p. DOI 10.1021/nl501870p.
4. Moerner, W. E. & Orrit, M. Illuminating single molecules in condensed matter. Sci. (New York, N.Y.) 283, 1670-6 (1999). URL http://www.ncbi.nlm.nih.gov/pubmed/10073924. DOI 10.1126/science.283.5408.1670.
5. Kozankiewicz, B. & Orrit, M. Single-molecule photophysics, from cryogenic to ambient conditions. Chem. Soc. Rev. 43, 1029-1043 (2014). URL http://xlink.rsc.org/?DOI=C3CS60165J. DOI 10.1039/C3CS60165J.
6. Li, W., Stein, S. C., Gregor, 1. & Enderlein, J. Ultra-stable and versatile widefield cryo-fluorescence microscope for single-molecule localization with sub-nanometer accuracy. Opt. express 23, 3770-83 (2015). URL http://www.osapublishing. org/viewmedia.cfm? uri=oe-23-3-3770&seq=0&html=true. DOI 10.1364/OE.23.003770.
7. Metzger, M. et al. Resolution enhancement for low-temperature scanning microscopy by cryo-immersion. Opt. Express 24, 13023 (2016). URL https://www.osapublishing.org/abstract.cfm?URI=oe-24-12-13023. DOI 10.1364/OE.24.013023.
8. Hell, S. W. & Wichmann, J. Breaking the Diffraction Resolution Limit By Stimulated-Emission—Stimulated-Emission-Depletion Fluorescence Microscopy. Opt. Lett. 19, 780-782 (1994). DOI 10.1364/OL.19.000780.
9. Betzig, E. et al. Imaging Intracellular Fluorescent Proteins at Nanometer Resolution. Sci. 313, 1642-1645 (2006). URL http://www.sciencemag.org/cgi/doi/10.1126/science. 1127344. DOI 10.1126/science.1127344.
10. Gustafsson, M. G. L. Surpassing the lateral resolution limit by a factor of two using structured illumination microscopy. J. Microsc. 198, 82-87 (2000). DOI 10.1046/j.1365-2818.2000.00710.x.
11. Sartori, A. et al. Correlative microscopy: Bridging the gap between fluorescence light microscopy and cryo-electron tomography. J. Struct. Biol. 160, 135-145 (2007). URL http://linkinghub.elsevier.com/retrieve/pii/S1047847707001724. DOI 10.1016/j.jsb. 2007.07.011.
12. Agronskaia, A. V. et al. Integrated fluorescence and transmission electron microscopy. J. Struct. Biol. 164, 183-189 (2008). URL http://dx.doi.org/10.1016/j.jsb.2008.07.003. DOI 10.1016/j.jsb.2008.07.003.
13. Smith, E. A. et al. Quantitatively Imaging Chromosomes by Correlated Cryo-Fluorescence and Soft X-Ray Tomographies. Biophys. J. 107, 1988-1996 (2014). URL http://linkinghub.elsevier.com/retrieve/pii/S0006349514009497. DOI 10.1016/j.bpj.2014. 09.011.
14. Chang, Y.-W. et al. Correlated cryogenic photoactivated localization microscopy and cryo-electron tomography. Nat. Methods 11, 737-739 (2014). URL http://www.nature.com/doifinder/10.1038/nmeth.2961. DOI 10.1038/nmeth.2961.
15. Liu, B. et al. Three-dimensional super-resolution protein localization correlated with vitrified cellular context. Sci. Reports 5, 13017 (2015). URL http://www.nature.com/articles/srep13017. DOI 10.1038/srep13017.
16. Nahmani, M., Lanahan, C., DeRosier, D. & Turrigiano, G. G. High-numerical-aperture cryogenic light microscopy for increased precision of superresolution reconstructions. Proc. Natl. Acad. Sci. 114, 3832-3836 (2017). URL http://www.pnas.org/lookup/doi/10.1073/pnas.1618206114. DOI 10.1073/pnas.1618206114.
17. Schorb, M. & Briggs, J. A. G. Correlated cryo-fluorescence and cryo-electron microscopy with high spatial precision and improved sensitivity. Ultramicroscopy 143, 24-32 (2014). URL http://dx.doi.org/10.1016/j.ultramic.2013.10.015. DOI 10.1016/j.ultramic.2013. 10.015.
18. Arnold, J. et al. Site-Specific Cryo-focused Ion Beam Sample Preparation Guided by 3D Correlative Microscopy. Biophys. J. 110, 860-869 (2016). URL http://linkinghub. elsevier.com/retrieve/pii/S0006349515011637. DOI 10.1016/j.bpj.2015.10.053.
19. Schorb, M. et al. New hardware and workflows for semi-automated correlative cryo-fluorescence and cryo-electron microscopy/tomography. J. Struct. Biol. 197, 83-93 (2017). URL http://linkinghub.elsevier.com/retrieve/pii/S1047847716301356. DOI 10.1016/j.jsb.2016.06.020.
20. Le Gros, M., McDermott, G., Uchida, M., Knoechel, C. & Larabell, C. High-aperture cryogenic light microscopy. J. Microsc. 235, 1-8 (2009). URL http://doi.wiley.com/10.1111/j.1365-2818.2009.03184.x. DOI10.1111/j.1365-2818.2009. 03184.x.
21. Smith, E. A. et al. Correlative cryogenic tomography of cells using light and soft x-rays. Ultramicroscopy 143, 33-40 (2014). URL http://dx.doi.org/10.1016/j.ultramic.2013.10.013. DOI 10.1016/j.ultramic.2013.10.013.
22. Edelstein, A. D. et al. Advanced methods of microscope control using μManager software. J. Biol. Methods 1, 10 (2014). URL http://www.jbmethods.org/jbm/article/view/36. DOI 10.14440/jbm.2014.36.
23. Schindelin, J. et al. Fiji: an open-source platform for biological-image analysis. Nat. Methods 9, 676-682 (2012). URL http://www.ncbi.nlm.nih.gov/pubmed/22743772. DOI 10.1038/nmeth.2019.
24. Sage, D. et al. DeconvolutionLab2: An open-source software for deconvolution microscopy. Methods 115, 28-41 (2017). URL http://linkinghub.elsevier.com/retrieve/pii/S1046202316305096. DOI 10.1016/j.ymeth.2016.12.015.
25. Thevenaz, P., Ruttimann, U. & Unser, M. A pyramid approach to subpixel registration based on intensity. IEEE Transactions on Image Process. 7, 27-41 (1998). URL http://ieeexplore.ieee.org/document/650848/. DOI 10.1109/83.650848.

26. Nasse, M. J. & Woehl, J. C. Realistic modeling of the illumination point spread function in confocal scanning optical microscopy. J. Opt. Soc. Am. A 27, 295 (2010). URL https://www.osapublishing.org/abstract.cfm?URI=josaa-27-2-295. DOI 10.1364/JOSAA.27.000295.

We claim:

1. A method of imaging a biological sample by light microscopy using an immersion objective, the method comprising imaging the biological sample by light microscopy, wherein cryogenic liquid consisting essentially of a hydrofluoroether is arranged as an immersion medium between the biological sample to be imaged and the immersion objection, wherein the immersion objective is immersed in the immersion medium.

2. The method of claim 1, wherein the hydrofluoroether is selected from ethoxy-nonafluorobutane ($C_4F_9OC_2H_5$) and methoxy-nonafluorobutane ($C_4F_9OCH_3$).

3. The method of claim 2, wherein the ethoxy-nonafluorobutane ($C_4F_9OC_2H_5$) is made of at least one of $(CF_3)_2CFCF_2OC_2H_5$ (CAS No. 163702-06-5) and $CF_3CF_2CF_2CF_2OC_2H_5$ (CAS No. 163702-05-4).

4. The method of claim 1, wherein the biological sample to be imaged is kept at a cryogenic temperature in the light microscopy.

5. The method of claim 4, wherein the biological sample to be imaged is kept at a cryogenic temperature in a range from −130° C. to −145° C.

6. The method of claim 1, wherein a heat flow is coupled into the immersion fluid at a front lens mount for a front lens of the immersion objective.

7. The method of claim 6, wherein a backside of the front lens is purged with dry nitrogen.

8. The method of claim 6, wherein the heat flow is directed into a cold stage carrying a sample holder holding the biological sample to be imaged.

9. The method of claim 1, wherein the biological sample to be imaged is covered with a cover slip, and wherein the immersion medium is arranged between the cover slip and the immersion objective.

* * * * *